US006997374B2

(12) United States Patent
Stradley et al.

(10) Patent No.: US 6,997,374 B2
(45) Date of Patent: Feb. 14, 2006

(54) APPARATUS FOR TESTING FOR PARTICULATE CONTAMINANTS IN DEPOSITORIES FOR MAIL-LIKE ARTICLES

(75) Inventors: Eugene C. Stradley, Owego, NY (US); John T. Swider, Port Crane, NY (US)

(73) Assignee: Lockheed Martin Corporation, Bethesda, MD (US)

( * ) Notice: Subject to any disclaimer, the term of this patent is extended or adjusted under 35 U.S.C. 154(b) by 6 days.

(21) Appl. No.: 10/307,531

(22) Filed: Nov. 27, 2002

(65) Prior Publication Data

US 2003/0119175 A1    Jun. 26, 2003

Related U.S. Application Data

(60) Provisional application No. 60/337,134, filed on Dec. 4, 2001, provisional application No. 60/334,239, filed on Nov. 29, 2001.

(51) Int. Cl.
*B65G 11/04* (2006.01)
(52) U.S. Cl. ..................... 232/45; 73/863.22
(58) Field of Classification Search ............... 232/45, 232/43.3; 422/119; 435/287.1; 73/824, 73/863.22; 902/17
See application file for complete search history.

(56) References Cited

U.S. PATENT DOCUMENTS

| | | |
|---|---|---|
| 3,942,357 A | 3/1976 | Jenkins |
| 3,998,101 A | 12/1976 | Bradshaw et al. |
| 4,111,049 A | 9/1978 | Lerner et al. |
| 4,360,108 A | 11/1982 | Logothetis |
| 4,372,482 A | 2/1983 | Clerigues |
| 4,580,440 A | 4/1986 | Reid et al. |
| 4,900,905 A | 2/1990 | Pusic |
| 4,940,887 A * | 7/1990 | Sheng-Jung ............... 235/381 |
| 4,987,767 A | 1/1991 | Corrigan et al. |
| 5,025,386 A | 6/1991 | Pusic |
| 5,273,183 A | 12/1993 | Tuttobene |
| 5,313,404 A * | 5/1994 | Wu .......................... 700/227 |
| 5,369,258 A | 11/1994 | Sansone et al. |
| 5,521,365 A | 5/1996 | Malatesta |
| 6,275,154 B1 | 8/2001 | Bennett et al. |
| 6,573,836 B1 * | 6/2003 | Gitis et al. ............... 73/863.22 |
| 6,742,703 B1 | 6/2004 | Esakov et al. |
| 2002/0124664 A1 * | 9/2002 | Call et al. ............... 73/863.22 |
| 2003/0085348 A1 | 5/2003 | Megerle |

(Continued)

FOREIGN PATENT DOCUMENTS

DE         19505474 A      8/1996

(Continued)

OTHER PUBLICATIONS

International Search Report, Nov. 17, 2003, PCT/US02/35984 (12078-154PCT).

(Continued)

*Primary Examiner*—William L. Miller
(74) *Attorney, Agent, or Firm*—Perkins Smith & Cohen LLP; Peter J. Borghetti; Harvey Kaye (57) ABSTRACT

An apparatus for testing for particulate contaminants in deposited mail-like articles includes an enclosure adapted for receiving deposited mail-like articles, a squeezing mechanism located within the enclosure and adapted for pressuring opposite flat sides of said deposited mail-like articles for expelling air along with any particulate matter from said deposited mail-like articles and into the enclosure, and a sensing apparatus operatively coupled to the enclosure and adapted for determining the presence of particulate contaminants in air expelled from the deposited mail-like articles. The apparatus may be embodied in a depository of an automated teller machine.

17 Claims, 5 Drawing Sheets

U.S. PATENT DOCUMENTS

| | | |
|---|---|---|
| 2003/0145664 A1 * | 8/2003 | Schwarz et al. ......... 73/863.22 |
| 2003/0152480 A1 | 8/2003 | Sham |
| 2003/0167740 A1 | 9/2003 | Murphy |
| 2003/0222132 A1 | 12/2003 | Esakov et al. |
| 2004/0020264 A1 * | 2/2004 | Megerle ................... 73/19.01 |

FOREIGN PATENT DOCUMENTS

| | | |
|---|---|---|
| GB | 608832 A | 9/1948 |
| GB | 2239864 A | 7/1991 |

OTHER PUBLICATIONS

WO 03/085373, Published PCT International Application, Publication Date Oct. 16, 2003, PCT/US02/35984 (12078-154PCT).

International Search Report, Nov. 20, 2003, PCT/US02/34514 (12078-198PCT).

WO 03/078957, Published PCT International Application, Publication Date Sep. 25, 2003, PCT/US02/34514 (12078-198PCT).

Lopez, et al., "System and Methods for Detecting Harmful Agents Within Contents of Mail.", United States Patent Application Publication No.: US 2002/0126008A1, Publication Date: Sep. 12, 2002, Filing Date: Oct. 31, 2001.

*U.S. Postal Service Emergency Preparedness Plan for Protecting Postal Employees and Postal Customers from Exposure to Biohazardous Material and for Ensuring Mail Security Against Bioterror Attacks; Mar. 6, 2002; published by USPS.

Provisional U.S. Appl. No. 60/334,239 filed Nov. 29, 2001. Applicant: Eugene Stradley. Title: Hazardous Material Characterizing and Warning System.

Provisional U.S. Appl. No. 60/337,134 filed Dec. 4, 2001. Applicants: John T. Swider et al. Title: Collection Box.

Provisional U.S. Appl. No. 60/344,846 filed Dec. 31, 2001. Applicant: William Harris. Title: Biomail System for the Detection of Pathogens.

Provisional U.S. Appl. No. 60/348,211 filed.

Copending U.S. Appl. No. 10/291,013 filed Nov. 8, 2002, Applicant: William Harris. Title: System For The Detection Of Pathogens In The Mail Stream.

Copending U.S. Appl. No. 10/309,541 filed Dec. 4, 2002. Applicants: Robert J. Felice et al. Title: Public Drop Box For Isolating Received Items.

Copending U.S. Appl. No. 10/208,960 filed Jul. 31, 2002. Applicant: Michael A. Wisniewski et al. Title: System and Method For Biohazard Detection Using Compression.

Copending U.S. Appl. No. 10/279,312 filed Oct. 24, 2002. Applicant: Clifford A. Megerle. Title: System And Method For Detecting Bio-hazardous Particulates In Mail Handling Systems.

* cited by examiner

APPARATUS FOR TESTING FOR PARTICULATE CONTAMINANTS IN DEPOSITORIES FOR MAIL-LIKE ARTICLES

RELATED APPLICATIONS

The present application claims priority for U.S. Provisional Patent Application Ser. No. 60/334,239, filed Nov. 29, 2001 and entitled HAZARDOUS MATERIAL CHARACTERIZING AND WARNING SYSTEM, and U.S. Provisional Patent Application Ser. No. 60/337,134, filed Dec. 4, 2001 and entitled COLLECTION BOX.

FIELD OF THE INVENTION

This invention relates generally to depositories for mail-like articles, and, more particularly to the detection of particulate contamination such as biological hazardous material, in mail-like articles received in such depositories.

BACKGROUND OF THE INVENTION

The recent incidents of anthrax-laced letters being transported through the United States Postal Service (USPS) facilities by unsuspecting mail handlers to unsuspecting recipients has alarmed the nation and the world. Currently, the tainted letters are discovered after the recipient accepts delivery or by alert postal employees noticing white powder that could be anthrax on mail parcels, sorting and distribution equipment, or themselves. There appear to be no current security devices or procedures that are available to intercept such letters at the earliest source of introduction into the USPS system, for example at the depository or drop boxes.

Many depository boxes already exist both in the US and around the world and they vary in form from stand-alone to built-in structures. Such depositories also take the form of ATM banking machines and less common, but still known, automated teller postal machines. Such postal machines are described in U.S. Pat. Nos. 4,900,905; 5,369,258; 4,940,887; 5,025,3386; 5,273,183 and 5,313,404.

Therefore, it would be desirable to have an apparatus which would provide the detection of particulate contamination in depository boxes of various types and applications.

SUMMARY OF THE INVENTION

Accordingly, one embodiment of the present invention provides an apparatus for testing for particulate contaminants in deposited mail-like articles comprising an enclosure adapted for receiving deposited mail-like articles, a squeezing mechanism located within said enclosure and adapted for pressuring opposite flat sides of the deposited mail-like articles for expelling air along with any particulate matter from the deposited mail-like articles and into the enclosure, and a sensing apparatus operatively coupled to the enclosure and adapted for determining the presence of particulate contaminants in air expelled from the deposited mail-like articles. The squeezing mechanism may comprise a pair of opposed rollers adapted to pass deposited mail-like articles there between and apply physical pressure to opposing sides of the deposited mail-like articles passing there between. The rollers may be located in a lower portion of the enclosure and the enclosure may be formed to gravitationally feed deposited mail-like articles to pass between the rollers. The apparatus may further comprise a pair of guides each having a planar surface oriented substantially parallel to the rollers, wherein the planar surfaces are oriented on opposing sides of any deposited mail-like articles and adapted to direct any deposited mail-like articles between the rollers. The enclosure may include an inlet port adapted for receiving deposited mail-like articles and a closure device adapted to close the inlet port while the squeezing mechanism is expelling air from the deposited mail-like articles. The inlet port may be of a size to admit only articles capable of being handled by the rollers. The enclosure may be adapted to hang from a wall with the depository port extending through the wall. The enclosure may be adapted to fit within either a mail box or an automated teller machine. The apparatus may further comprise a controller adapted to activate the squeezing mechanism and the sensing apparatus in response to a detection of mail-like articles in the enclosure. The apparatus may also comprise means for communicating an alarm signal in response to a detection of particulate contamination in the enclosure. The apparatus may also further comprise a communication device adapted to signal information concerning the apparatus.

In another embodiment, the present invention provides a depository for mail-like articles, comprising an enclosure adapted for receiving deposited mail-like articles, a depository port adapted for passing deposited mail-like articles into the enclosure, a squeezing mechanism located in the enclosure and adapted for pressuring opposite flat sides of said deposited mail-like articles for expelling air along with particulate matter from the deposited mail-like articles into the enclosure, and a sensing apparatus operatively coupled to the enclosure and adapted for determining the presence of particulate contaminants in air expelled from the deposited mail-like articles. Further refinements may be made to this depository in accordance with the refinements discussed above for the apparatus.

In yet another embodiment, the present invention provides an automated teller machine for receiving mail-like articles deposited therein, comprising an enclosure adapted for receiving deposited mail-like articles, a depository port adapted for passing deposited mail-like articles into the enclosure, a squeezing mechanism located in the enclosure and adapted for pressuring opposite flat sides of said deposited mail-like articles for expelling air along with particulate matter from the deposited mail-like articles into the enclosure, and a sensing apparatus operatively coupled to the enclosure and adapted for determining the presence of particulate contaminants in any air expelled from the deposited mail-like articles. Further refinements may be made to this automated teller machine in accordance with the refinements discussed above for the apparatus.

BRIEF DESCRIPTION OF THE DRAWINGS

The present invention is illustratively shown and described in reference to the appended drawings, in which.

DETAILED DESCRIPTION OF THE DRAWINGS

Figure 1:
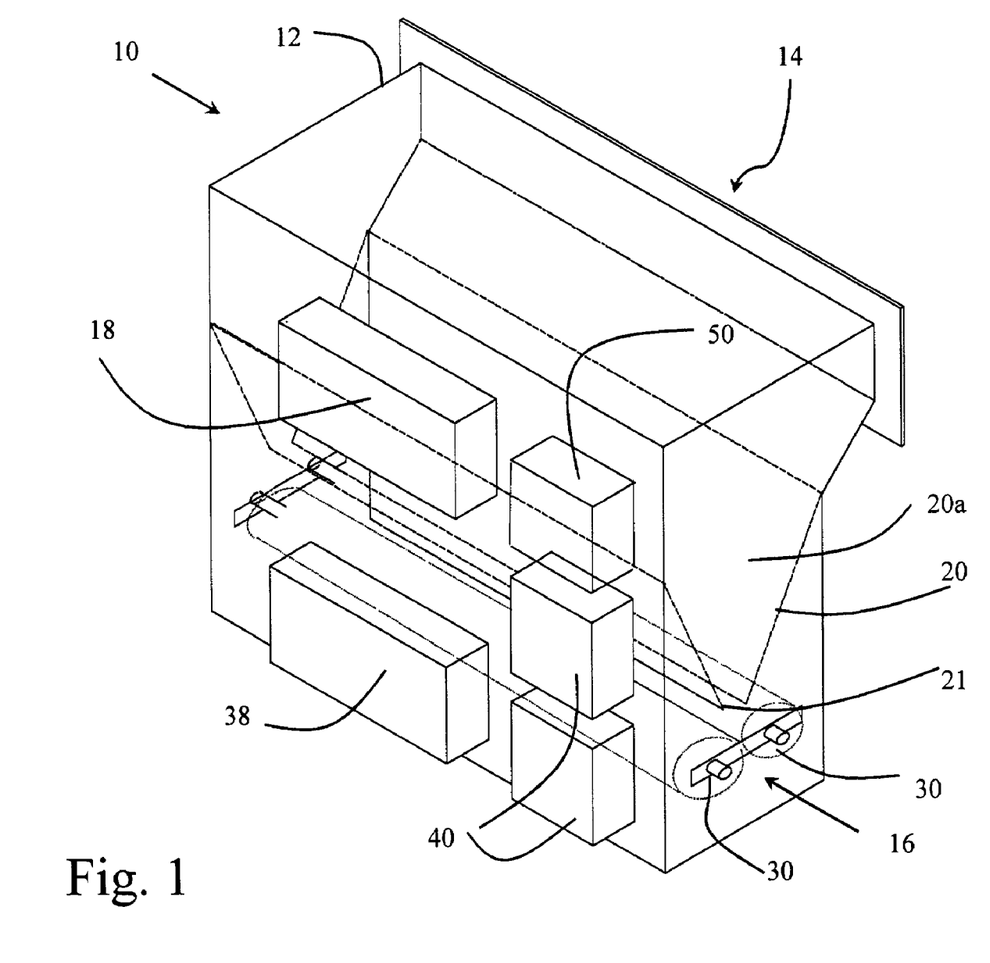
FIG. 1 is a perspective view of an apparatus constructed in accordance with one embodiment of the present invention.
Figure 2:
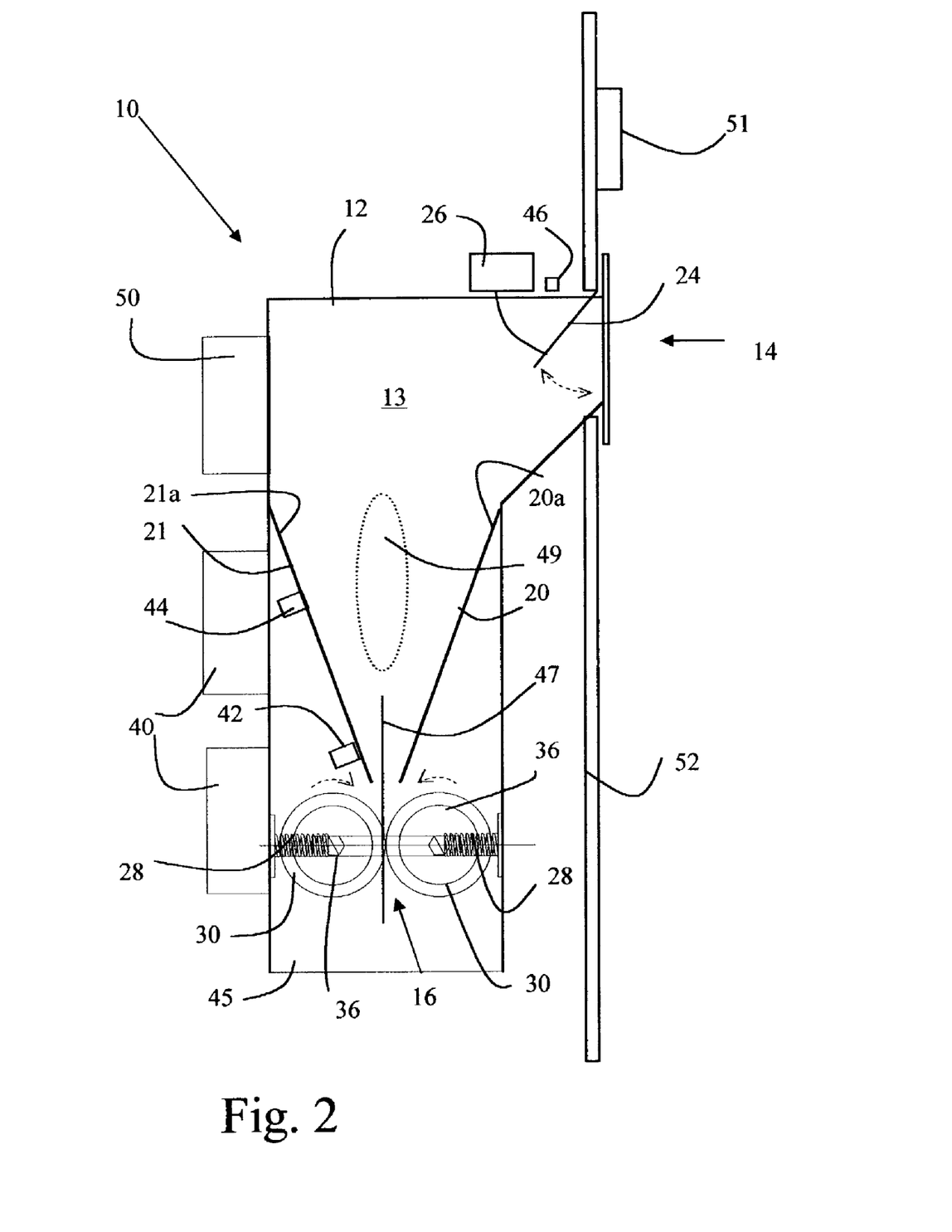
FIG. 2 is an exposed side view of the apparatus of FIG. 1.

FIGS. 1 and 2 show an apparatus 10 from perspective and exposed end views, respectively, which apparatus 10 is constructed in accordance with one embodiment of the present invention. Apparatus 10 generally includes an enclosure 12 forming a chamber 13 and having a depository port 14 configured to pass deposited mail-like articles into chamber 13. The term "mail-like articles" is used herein to describe anything similar to an envelope or mail flat having opposed flat sides. A squeezing mechanism 16 is located within chamber 13 and configured for pressuring deposited mail-like articles from opposing flat sides for expelling air located therein along with any particulate matter that might be located in the deposited mail-like articles. A sensing apparatus 18 is operatively coupled to withdraw air samples from chamber 13 and adapted for determining the presence of particulate contaminants in those air samples.

Squeezing mechanism 16 is located below depository port 14 to provide gravitational feeding of deposited mail-like articles to mechanism 16. A pair of guides 20, 21 are located for properly orienting deposited mail like articles with respect to squeezing mechanism 16. Enclosure 12 may further include a closeable door 24 (FIG. 2) adapted to cover depository port 14 under the control of a suitable closing mechanism 26 (FIG. 2).

Squeezing mechanism 16 preferably includes a pair of parallel, horizontally oriented rollers 30. Rollers 30 are in substantial contact over their entire length and are movably mounted on mounts 28 under spring bias towards each other. Mounts 28 are adapted to allow rollers 30 to move away from each other in opposing directions due to the thickness of any articles passing between rollers 30. This arrangement provides a variable gap between rollers 30, which gap is automatically adjusted to the varying thicknesses of different mail-like articles, while still providing inward pressure on opposing sides of all such mail like articles. Included within rollers 30 is a separate drive motor 36. The physical characteristics of the preferred pinch rollers 30 are 1.9" in diameter and 17" long having a non-slip ⅛" thick coating. One pinch roller which may be used is manufactured by Sparks Belting Company under part number MRD-48-412-40-VO, though any conventional pinch roller assembly is suitable.

Guides 20, 21 are located to direct deposited mail-like articles between rollers 30. Guides 20, 21 each includes a respective planar surface 20a, 21a, which is oriented substantially parallel to the axes of rotation of rollers 30 to thereby align deposited mail-like articles with rollers 30 and the line of contact between rollers 30. Planar surfaces 20a, 21a are located or oriented on opposing sides of any deposited mail-like articles to direct any deposited mail-like articles between rollers 30.

Rollers 30 are powered by a 24 volt power supply 38 and controlled through drive motors 36 by individual controllers 40. Controllers 40 may work in conjunction with one or more sensors 42, 44, 46. Sensors 42, 44, 46 may be located in various appropriate positions within enclosure 12. Sensor 42 is shown in a position for sensing mail-like articles located in close proximity to rollers 30. Sensor 44 may be located somewhat higher than sensor 42 to detect mail-like articles which may have jammed between the guides 20 and 21. Sensor 46 may be located to sense the opening of door 24 or otherwise to detect the deposit of mail-like articles through depository port 14. Any other suitable combination of sensors and locations thereof may also be used. Such sensors may be embodied by any suitable device, such as an infrared sensor or micro switches. In one apparatus, sensors 42 and 44 are a photo reflective type PMP device manufactured by Cutler Hammer part number 14156RDP1 7B1, however other conventional photo sensors or mechanical switches may be suitable.

The preferred particulate sensing apparatus 18 is the BIONI sensor manufactured by Pacific Scientific Instruments. An alternative particulate sensor apparatus 18 is the Biological Aerosol Warning Systems, BAWS I, developed by Lockheed Martin Corporation, the assignee of this application. Typically, BAWS units are deployed around the perimeter of a facility to detect and analyze airborne particles for biological contaminants. Though the BIONI sensor is disclosed in the preferred embodiment, other available particulate sensors may also be adapted for use. Of particular significance is the ability of such sensors to detect particulate contaminants in the size range of 2 to 10 microns.

Apparatus 10 may further include a suitable microprocessor control 50 for handling overall management of apparatus 10 and communications with a remote monitoring station. Alternatively, controllers 40 may take various forms such as a microprocessor, a programmable logic controller, or even a simple mechanical controller adapted to perform the necessary control functions. In operation, the deposit of mail-like articles through depository port 14 is detected by sensors 46, 44 or 42 and sensing apparatus 18 is activated responsively. Deposited mail-like articles are fed by gravity and guides 20, 21 between rollers 30 and their presence is detected by sensor 42. This detection may optionally cause closure of door 24 by closing mechanism 26 to thereby prevent expelling of any particulate contaminants outside of chamber 13. This detection also causes drive motors 36 and rollers 30 to be activated for counter rotation thereby driving mail-like article 47 between rollers 30. The drive force of rollers 30 draws mail-like article 47 there between, causing the spring bias of mounts 28 to adjust the spacing between rollers 30 to accommodate the normal range of thicknesses for deposited mail-like articles, while still applying sufficient force on opposing sides of the mail-like articles to expel air. Excess air located within mail-like article 47 is forced to the top of mail-like article 47 and expelled as a plume 49 into chamber 13. Testing apparatus 18 may be adapted to withdraw air samples from various locations within chamber 13 and thereby sample a variety of different plumes. This will help compensate for envelopes which may be more porous or may not contain much excess air, thus reducing the size of a plume that would be created under different conditions. Once past rollers 30, mail-like articles drop through the open bottom 45 of enclosure 12, which may optionally include a normally closed portal to reduce the introduction of external contamination into chamber 13. Rollers 30 and sensing apparatus 18 may be deactivated in response to any suitable control arrangement, such as sensors or timers.

Controller 40 may also be programmed to sense a jam of mail-like articles between guides 20, 21, for example when sensor 42 does not indicate the presence of a mail-like articles while sensor 44 does indicate such presence. Under such jammed conditions controller 40 would typically be programmed to request service of the apparatus 10. Optionally, driven, anti-jam rollers (not shown) may be provided at the height of sensor 44 and be activated by controller 40 under jam conditions. To further reduce the possibility of jamming, the size of depository port 14 may be limited to the maximum size of mail-like articles which can be handled by squeezing mechanism 16. In one embodiment, a ¾" width is used for depository port 14 to admit articles of comparable thickness.

The apparatus 10 described above is sufficiently robust so that mail-like articles may be deposited in bunches or groups so long as such deposits fit through depository port 14. Rollers 30 can adjust to different thicknesses and thus may squeeze more than one envelope or mail-like article at a time. The result for each mail-like article will be the same as that described above, excess air will be expelled into chamber 13.

In conjunction with microprocessor control 50, apparatus 10 may also include a suitable display device 51 (FIG. 2) operatively coupled to microprocessor control 50, which display device 51 may be used by controller 40 to provide guidance to potential depositors of mail-like articles. Such guidance may include messages such as "Deposit Mail", "Out of Service", or "Danger Please Notify Authorities". Display device 51 may further include an audio speaker for providing similar messages.

Enclosure 12 is adapted for installation behind a wall 52 with depository port 14 extending through an opening in such wall. Wall 52 may be structural or simply part of a large apparatus. In this form, apparatus 10 is ideally suited for use in post office lobbies and other publicly accessible buildings in which wall mounted postal slots are installed for public convenience.

Figure 3:
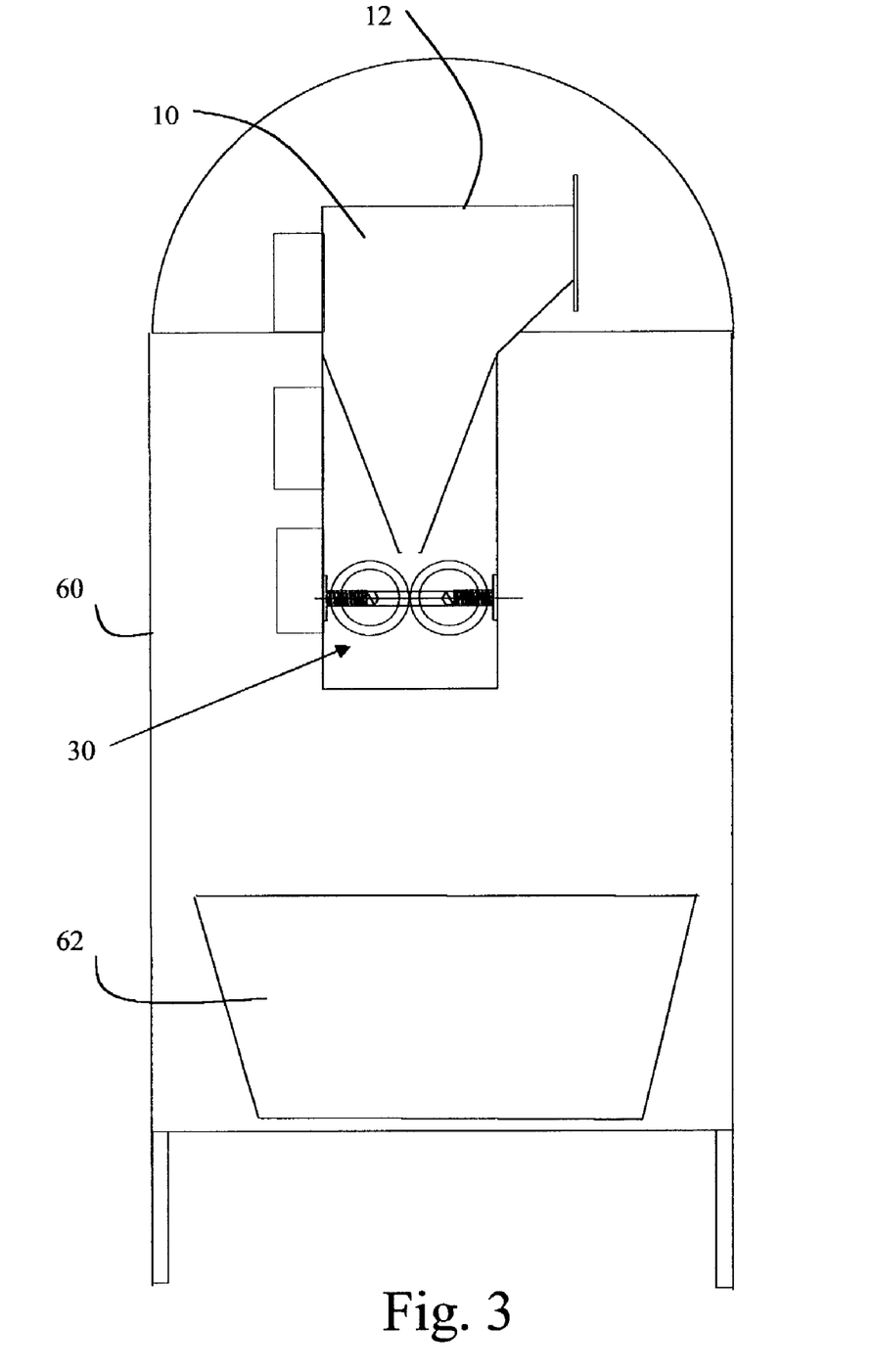
FIG. 3 is a diagrammatic view of a postal depository constructed in accordance with another embodiment of the present invention.

As shown in FIG. 3, apparatus 10 is also adapted for installation within existing depository boxes, such as mail box 60. Mail which has passed between rollers 30 drops from the enclosure 12 into a receptacle such as a standard mail flat tray 62.

Figure 4:
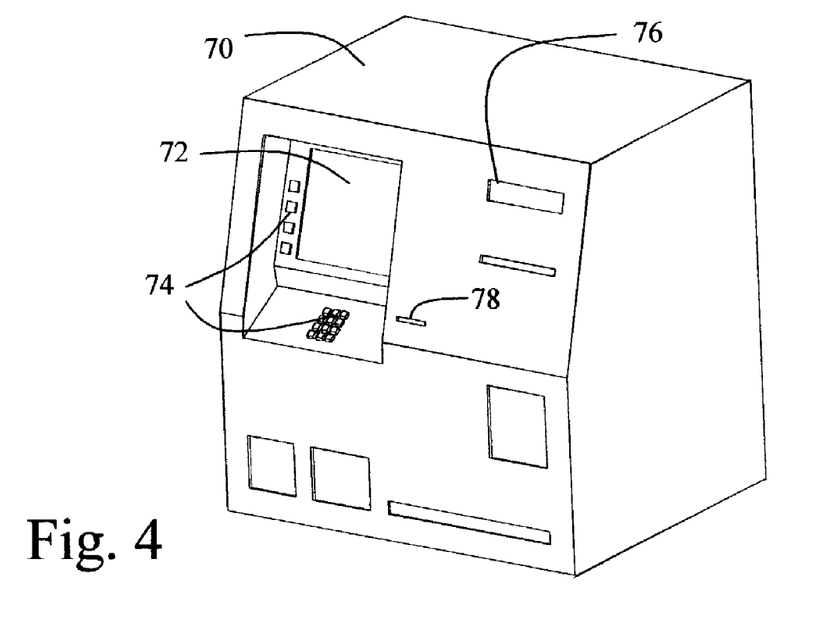
FIG. 4 is a perspective view of an automated teller machine constructed in accordance with yet another embodiment of the present invention.

FIG. 4 shows another embodiment of the present invention, in the form of an automated teller machine 70, which provides the additional security of user identification through the use of magnetic card readers and video surveillance. Automated teller machine 70 performs teller like services in which mail-like articles are to be received under some interaction with a depositor, such as banking or postal services. Such machines 70 typically include a visual display 72 for providing information to depositors and an input mechanism 74, such as keys, for receiving responses from such depositors. Machine 70 necessarily includes a depository port 76 for receiving mail-like articles, and may optionally include a magnetic card reader behind a slot 78.

Figure 5:
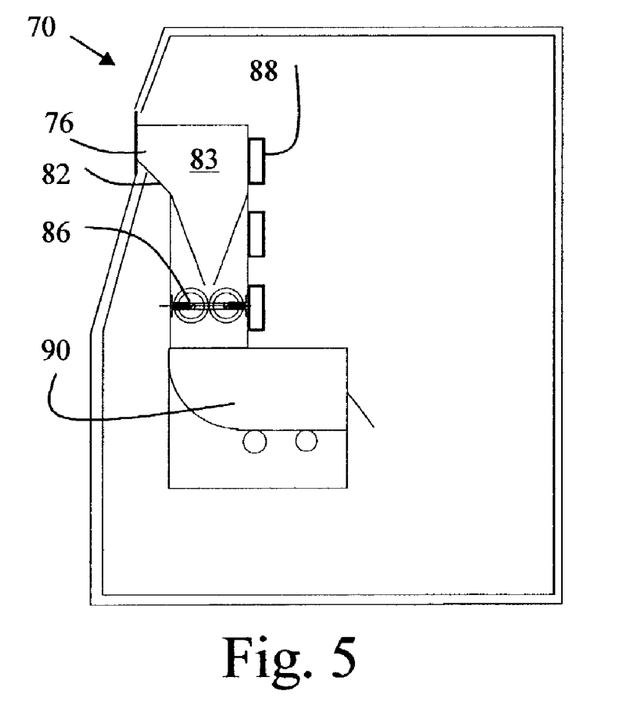
FIG. 5 is an exposed side view of the apparatus of FIG. 4.

FIG. 5 shows a representational cut-away diagram of the side of machine 70 in which an enclosure 82 is depicted in a manner similar to that of FIG. 2. Enclosure 82 includes a depository port 76 which connects to a chamber 83. Chamber 83 leads directly to a squeezing mechanism 86, which may be constructed similar to squeezing mechanism 16 (FIGS. 1 and 2). After deposited mail-like articles pass squeezing mechanism 86, they are temporarily held in a chamber 90 pending the results from a sensing apparatus 88. This pause enables the capture and retention of any detected particle contaminants without the pollution of other portions of machine 70. During testing, a depositor may be queried for relevant information. After a successful test, a mail-like article is forwarded for other processing, which may include weighing, franking and bar coding for mail. The details of such further mail processing are known through a variety of prior art patents as cited above. Users of such automated teller machines 70 enjoy an extra layer of security in knowing that previous users have gone through the same monitored process.

Figure 6:
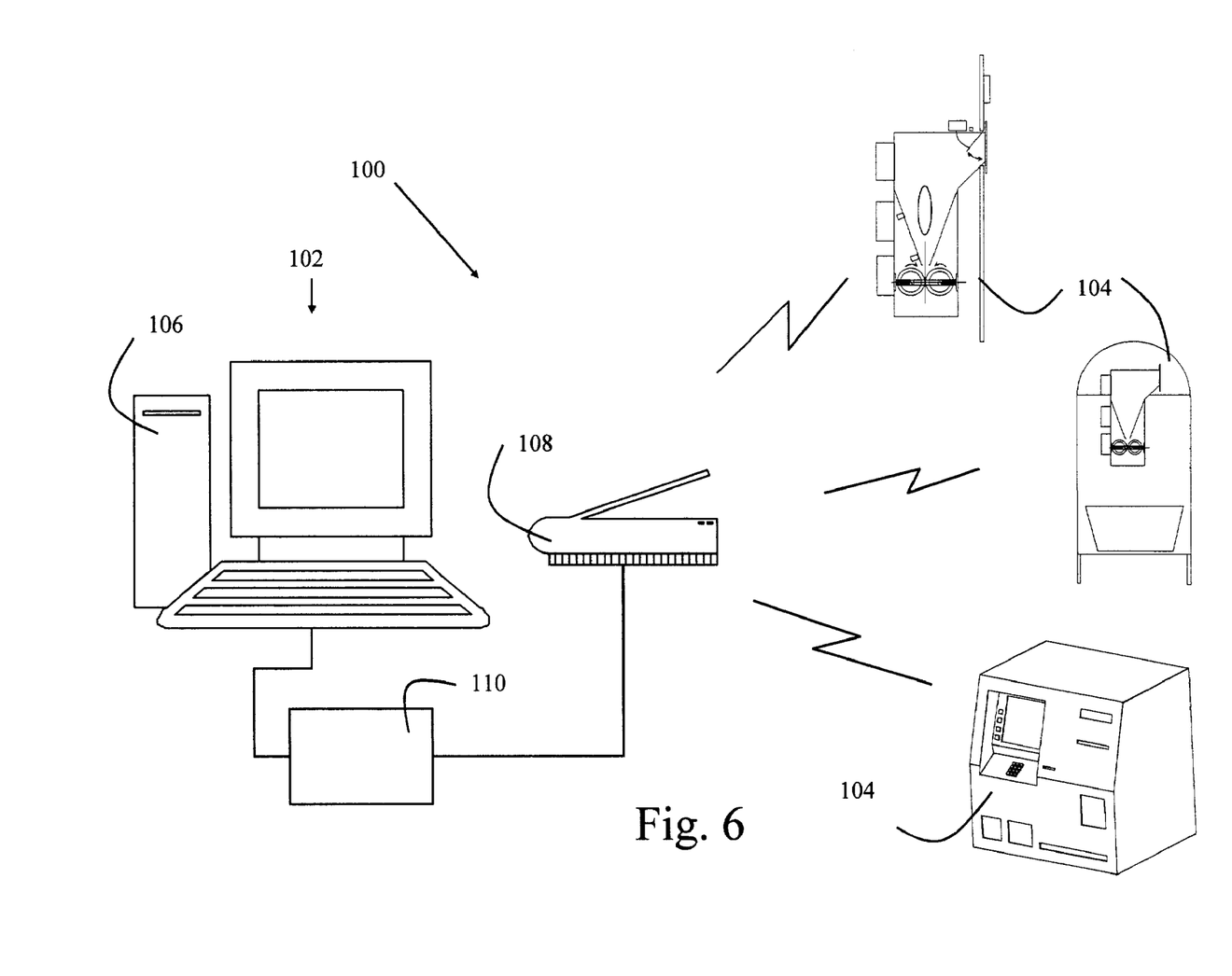
FIG. 6 is a diagram of a data collection system which may be used in conjunction with the embodiments of the present application.

FIG. 6 shows an application of the present invention to a monitoring network 100 generally including a central data collection station 102 in communication with a multiplicity of depository devices 104 equipped with an apparatus in accordance with the present invention. Data collection station 102 would typically include a computer 106, communication equipment 108 and an interface 110 between computer 106 and communication equipment 108. Communication equipment 108 is shown to use wireless signals, however any other suitable communications, such as wired or optical, may also be employed. Computer 106 is programmed to monitor and store data collected from the depository devices 104 and to identified any abnormal conditions such as the detection of particulate contamination, depository service requirements, or any other anomalies which might be reported from depository devices 104. Such a monitoring network 100 has been developed by Lockheed Martin Corporation, the assignee of the present application.

The present invention is illustratively described above in reference to the disclosed embodiments. Various modifications and changes may be made to the disclosed embodiments by persons skilled in the art without departing from the scope of the present invention as defined in the appended claims.

What is claimed is:

1. An apparatus for testing for particulate contaminants in deposited mail-like articles, comprising:
   an enclosure adapted for receiving deposited mail-like articles:
   a squeezing mechanism located within said enclosure and adapted for pressuring opposite flat sides of the deposited mail-like articles for expelling air along with any particulate matter from the deposited mail-like articles and into said enclosure; and
   a sensing apparatus operatively coupled to said enclosure and adapted for determining the presence of particulate contaminants in air expelled from the deposited mail-like articles,
   wherein said squeezing mechanism comprises a pair of opposed rollers located in a lower portion of said enclosure and adapted to pass deposited mail-like articles there between, and
   further wherein said enclosure is formed to gravitationally feed deposited mail-like articles to said rollers.

2. The apparatus of claim 1, further comprising a pair of guides each having a planar surface oriented substantially parallel to said rollers, wherein said planar surfaces are oriented on opposing sides of any deposited mail-like articles and adapted to direct any deposited mail-like articles between said rollers.

3. The apparatus of claim 1, wherein said enclosure includes an inlet port adapted for receiving deposited mail-like articles and a closure device adapted to close said inlet port while said squeezing mechanism is expelling air from said deposited mail-like articles.

4. The apparatus of claim 3, wherein said inlet port is of a size to admit only articles capable of being handled by said rollers.

5. The apparatus of claim 3, wherein said enclosure is adapted to hang from a wall with said inlet port extending through the wall.

6. The apparatus of claim 1, wherein said enclosure is adapted to fit within a mail box or within an automated teller machine.

7. The apparatus of claim 1, further comprising a controller adapted to activate said squeezing mechanism and said sensing apparatus in response to a detection of mail like articles in said enclosure.

8. The apparatus of claim 1, further comprising means for generating an alarm signal in response to a detection of particulate contamination in said enclosure.

9. The apparatus of claim 1, further comprising a communication device adapted to signal information concerning said apparatus.

10. A depository for mail-like articles, comprising:
an enclosure adapted for receiving deposited mail-like articles;
a depository port adapted for passing deposited mail-like articles into said enclosure;
a squeezing mechanism located in said enclosure and adapted for pressuring opposite flat sides of the deposited mail-like articles for expelling air along with particulate matter from the deposited mail-like articles into said enclosure;
wherein said depository port includes a closure device adapted to close said inlet port while said squeezing mechanism is expelling air from said deposited mail-like articles; and
a sensing apparatus operatively coupled to said enclosure and adapted for determining the presence of particulate contaminants in air expelled from the deposited mail-like articles,
further wherein said squeezing mechanism comprises a pair of opposed rollers adapted to pass deposited mail-like articles there between and apply physical pressure to opposing sides of the deposited mail-like articles passing there between.

11. The depository of claim 10, wherein said rollers are located in a lower portion of said enclosure and further wherein said enclosure is formed to gravitationally feed deposited mail-like articles to said rollers.

12. The depository of claim 11, further comprising a pair of guides each having a planar surface oriented substantially parallel to said rollers, wherein said planar surfaces are oriented on opposing sides of any deposited mail-like articles and adapted to direct any deposited mail-like articles between said rollers.

13. The depository of claim 10, further comprising a communication device adapted to signal information concerning said depository.

14. The depository of claim 13, wherein said communication device includes a display device adapted to advise potential depositors concerning operating conditions and further includes an alarm for signaling detection of particulate contamination.

15. An automated teller machine for receiving mail-like articles deposited therein, comprising:
an enclosure adapted for receiving deposited mail-like articles;
a depository port adapted for passing deposited mail-like articles into said enclosure;
a squeezing mechanism located in said enclosure and adapted for pressuring opposite flat sides of the deposited mail-like articles for expelling air along with particulate matter from the deposited mail-like articles into said enclosure; and
a sensing apparatus operatively coupled to said enclosure and adapted for determining the presence of particulate contaminants in any air expelled from the deposited mail-like articles,
wherein said squeezing mechanism comprises a pair of opposed rollers adapted to pass deposited mail-like articles there between and located in a lower portion of said enclosure, and further wherein said enclosure is formed to gravitationally feed deposited mail-like articles between said rollers.

16. An apparatus for testing for particulate contaminants in deposited mail-like articles, comprising:
an enclosure adapted for receiving deposited mail-like articles: a squeezing mechanism located within said enclosure and adapted for pressuring opposite flat sides of the deposited mail-like articles for expelling air along with any particulate matter from the deposited mail-like articles and into said enclosure; and
a sensing apparatus operatively coupled to said enclosure and adapted for determining the presence of particulate contaminants in air expelled from the deposited mail-like articles,
wherein said enclosure includes an inlet port adapted for receiving deposited mail-like articles, and
further wherein said enclosure hangs from a wall with said inlet port extending through the wall.

17. The apparatus of claim 16, further comprising
a communication device adapted to signal information concerning said depository, said communication device including a display device adapted to advise potential depositors concerning operating conditions and further including an alarm for signaling detection of particulate contamination.

* * * * *